(12) United States Patent
Teughels et al.

(10) Patent No.: US 8,283,926 B2
(45) Date of Patent: Oct. 9, 2012

(54) MAGNETIC RESONANCE IMAGING OF SINGLE DOMAIN NANOPARTICLES

(75) Inventors: Stephanie Teughels, Herent (BE); Peter Vaes, Rijmenam (BE)

(73) Assignee: IMEC, Leuven (BE)

( * ) Notice: Subject to any disclaimer, the term of this patent is extended or adjusted under 35 U.S.C. 154(b) by 0 days.

(21) Appl. No.: 12/959,310

(22) Filed: Dec. 2, 2010

(65) Prior Publication Data

US 2011/0148414 A1    Jun. 23, 2011

Related U.S. Application Data

(63) Continuation of application No. PCT/EP2009/062722, filed on Sep. 30, 2009.

(60) Provisional application No. 61/101,374, filed on Sep. 30, 2008.

(30) Foreign Application Priority Data

Apr. 17, 2009   (GB) .................................. 0906644.0

(51) Int. Cl.
   *G01V 3/00*   (2006.01)
(52) U.S. Cl. ........................................ 324/316; 324/318
(58) Field of Classification Search .................. 324/316, 324/318, 322, 300
   See application file for complete search history.

(56) References Cited

U.S. PATENT DOCUMENTS

| | | | |
|---|---|---|---|
| 4,940,966 A | 7/1990 | Pettigrew et al. | |
| 6,472,874 B1 * | 10/2002 | Chandrakumar et al. | .... 324/316 |
| 6,924,150 B1 | 8/2005 | Xiang et al. | |
| 7,483,732 B2 * | 1/2009 | Zhong et al. | .................. 600/423 |
| 2004/0026028 A1 | 2/2004 | Kirsten et al. | |
| 2004/0138554 A1 | 7/2004 | Dimmer et al. | |
| 2005/0118102 A1 * | 6/2005 | Xiang et al. | ................. 424/9.34 |
| 2005/0179552 A1 | 8/2005 | Shoji et al. | |

FOREIGN PATENT DOCUMENTS

| | | |
|---|---|---|
| DE | 10118683 | 10/2002 |
| EP | 1860458 | 11/2007 |

OTHER PUBLICATIONS

International Search Report and Written Opinion dated Jan. 26, 2010 for PCT/EP2009/062722.
International Preliminary Report on Patentability dated Sep. 7, 2010 for PCT/EP2008/062722. Shellock, Frank; Magnetic Resonance Procedures: Health Effects and Safety; CRC Press; 2001.
Moreland et al; Ferromagnetic resonance spectroscopy with a micromechanical calorimeter sensor; Review of Scientific Instruments; vol. 71, No. 8; Aug. 2000.
Gleich et al; Tomographic imaging using the nonlinear response of magnetic particles, Nature, vol. 435, pp. 1214-1217, Jun. 30, 2005.

* cited by examiner

*Primary Examiner* — Louis Arana
(74) *Attorney, Agent, or Firm* — Knobbe, Martens, Olson & Bear LLP

(57) ABSTRACT

A method and system are disclosed for gathering information about an object including single domain particles which have a diameter in the range of about 5 to 80 nm. In one aspect, a method includes generating a static magnetic field of less than about 0.1 Tesla on the object and generating an RF energy, pulsed or continuous wave, so as to generate electron paramagnetic resonance of the single domain particles. The method also includes detecting the electron paramagnetic resonance of the single domain particles in the form of an image of the object. The single domain particles may have a predetermined diameter and a predetermined saturation magnetization and the applied magnetic field may be such that the single domain particles reach a magnetization being at least about 10% of the saturation magnetization. The method may be used for detecting tags in an object and for activating tags.

21 Claims, 9 Drawing Sheets

MAGNETIC RESONANCE IMAGING OF SINGLE DOMAIN NANOPARTICLES

CROSS REFERENCE TO RELATED APPLICATIONS

This application is a continuation of PCT Application No. PCT/EP2009/062722, filed Sep. 30, 2009, which claims priority under 35 U.S.C. §119(e) to U.S. provisional patent application 61/101,374 filed on Sep. 30, 2008. Each of the above applications is incorporated herein by reference in its entirety.

BACKGROUND OF THE INVENTION

1. Field of the Invention

This invention relates to detection systems using either continuous wave or pulsed radio frequency energy to detect magnetic resonance responses, to receivers for such systems, and to corresponding methods and software for carrying out the methods, and to methods of using continuous wave or pulsed radio frequency energy to activate tags having a magnetic resonance response and to tags for such apparatus and methods.

2. Description of the Related Technology

Magnetic resonance Imaging (MRI) is a well-known technique to produce high quality tomographic images (2D slices or 3D images) inside the human body. MRI is based on the principles of nuclear magnetic resonance (NMR). MRI commonly uses DC magnetic fields of 1 Tesla (T) to 3 Tesla (T) to magnetize the nuclei. Electromagnetic waves in a narrow-band frequency range are selected to identify resonant properties (frequencies, relaxation times) of specific nuclei. For example, protons are commonly used for imaging of human organs due to the high concentration of H2O in the body with typical resonant frequencies close to 42 MHz at 1 T. Other nucleus Larmor frequencies are in the range 50 KHz-100 MHz and the entire frequency spectrum of interest in those imaging applications is of the order 10 kHz-1 MHz, which is an extremely narrow band, and the hardware is optimized towards generating and receiving this single-frequency e.g. a heterodyne detector matched to the frequency band of the source. In some MRI experiments a complex pulse sequence of narrowband RF waves is used to manipulate the phase of the nuclei so as to create a specific type of NMR signal. The pulse should rotate the spins of the nuclei over exactly 90 or 180 degrees and has to be tuned together with the nuclei resonance and can be 1-2000 microseconds.

In order for any tissue to be visible in an MRI image there must be contrast in the emitted signal (amplitude/phase/frequency) of the nuclei in the targeted and the adjacent tissue. This contrast can originate from differences in nuclear spin relaxation time, nucleus concentration or density. A contrast medium is often introduced into the body to enhance the contrast between the tissues by differential uptake. Paramagnetic or single domain (including super-paramagnetic particles) particles are often used as contrast agents that create oscillating fields when they tumble through a water environment, thereby changing the relaxation times ($T_1$ and $T_2$) of the tissues by introducing randomly fluctuating magnetic fields near the nucleus of interest, e.g. some tumor cells have a greater Gd uptake than the surrounding tissues, thereby decreasing $T_1$ and resulting in strong contrast of tumors in MRI scans. Ferromagnetic resonance (FMR) imaging is a technique which is used for imaging ferromagnetic materials. In U.S. Pat. No. 6,924,150 a technique for narrow band radio frequency FMR imaging was proposed. Since the human body does not contain such properties by nature, FMR imaging was never considered for biomedicine applications. In a ferromagnetic material, the ferromagnetic resonance (FMR) signal is much stronger than NMR or other resonances due to the very high spin density and strong exchange coupling between the spins. The same exchange coupling also causes suppression of spin-spin relaxation such that the spin-lattice relaxation will dominate the total relaxation time.

Ferro- and ferri-magnetic nanoparticles are known for use as contrast agent in MR (Magnetic Resonance) imaging applications (at low frequencies) and for FMR imaging (U.S. Pat. No. 6,924,150).

In Nature 435 (2005) 1214, Gleich and Weizenecker describe a method of directly using magnetic particle imaging based on the nonlinearity of magnetization curves of ferromagnetic materials and the fact that the particle magnetization saturates at some magnetic field strength. The imaging techniques uses a time independent field that vanishes in the centre and increases in magnitude at the edges, such that only particles at that centre position are not saturated and respond to a second stimulus. Imaging is obtained by steering the central point of the time independent field through the volume of interest. The risks of using conventional MRI techniques are disclosed in "Magnetic Resonance Procedures: Health Effects and Society", Ed. F. G. Shellock, CRC Press, 2001.

The use of magnetic medium to act as identification tags is already applied in magnetic RF-ID tags that consist of a magnetic medium which is detected when the article to which it is attached passes through a detection system, which emits an alternating narrow-band magnetic interrogation field of 50 Hz-100 KHz. Several patents (e.g. U.S. Pat. No. 4,940,966) discuss inventive magnetic bar coding or tagging principles based on distinctive physical parameters (e.g. shape, magnetic material, distance and orientation with respect to another tag). UWB radar technology is known for positioning of large articles (e.g. car identification, through wall vision) and motion sensing.

Magnetic RF-ID tags are known in U.S. Pat. No. 4,940,966 and implantable resonator circuits (LC tanks) including magnetic material in the inductor are shown in US2004138554 and US2005179552.

Magnetothermia (heating/destroying of cells) by specific uptake of nanoparticles and selective heating using AC magnetic fields below approx. 1 MHz is known. Heating of substrates by electromagnetic radiation at ferromagnetic resonance frequencies (1-300 GHz) is shown in US2004026028 and in [John Moreland, et al., Rev. of Sci. Instr., Vol 71 p 3088].

SUMMARY OF CERTAIN INVENTIVE ASPECTS

Certain inventive aspects relate to methods and systems for gathering information about an object using a resonance technique. It is an advantage of certain embodiments according to the present invention that no reaction is required between particles and the object for allowing detection or imaging. It is an advantage of certain embodiments according to the present invention that detecting may be obtained. It is an advantage of certain embodiments according to the present invention that accurate imaging can be obtained using an imaging technique based on detecting electron paramagnetic resonance of single domain particles. It is an advantage of certain embodiments according to the present invention that fast imaging can be obtained using a technique based on detecting electron paramagnetic resonance of single domain particles. Certain inventive aspects of embodiments of the present invention relate to improved apparatus or methods for detection using continuous wave or pulsed radio frequency energy, to provide receivers for such systems, and/or corresponding methods and software for carrying out the methods. Certain inventive aspects of embodiments of the present invention relate to methods of using continuous wave or pulsed radio frequency energy to activate tags and/or tags for such apparatus and methods.

A first inventive aspect relates to a method of gathering information about an object, the object including single domain particles having a diameter in the range of about 5 nm to 80 nm, e.g. in a range of 5 nm to 80 nm, the method comprising applying to the object to a static magnetic field of less than about 0.1 Tesla, e.g. lower than about 0.1 Tesla, applying a RF energy to the object at a frequency to generate Electron paramagnetic resonance (EPR) of the single domain particles, and detecting the EPR of the single domain particles.

Another inventive aspect relates to a method for gathering information about an object, the object including single domain particles having a diameter in the range of about 5 nm to 80 nm, the method comprising detecting Electron paramagnetic resonance (EPR) of the single domain particles upon interaction of the object with a static magnetic field of less than about 0.1 Tesla and with RF energy at a frequency to generate EPR of the single domain particles. Although interaction of the object with the magnetic field or the RF energy may not be part of the method, the method may comprise applying to the object a static magnetic field of less than about 0.1 Tesla and the method also may comprise applying an RF energy to the object at a frequency to generate Electron Paramagnetic Resonance of the single domain particles.

Detecting the EPR of single domain particles may be performed by detecting the EPR of single domain particles in the form of an image of the object. Such an image may be a single pixel image or a multi-pixel image. Detecting in the form of an image may be detecting in the form of a volumetric image of the object. With a volumetric image of the object, 2-dimensional (2D) as well as three dimensional images may be envisaged. The method thus may be adapted for obtaining an at least 2-dimensional image.

In an embodiment, the single domain particles can have a particle diameter between 5 nm and 100 nm, e.g. between about 5 nm and 80 nm, e.g. in a range of 5 nm to 80 nm, between about 5 nm and 60 nm, e.g. in a range of 5 nm to 60 nm, between about 10 nm and 30 nm, e.g. in a range of 5 nm to 30 nm, between 40 nm and 60 nm e.g. in a range of 40 nm to 60 nm. In an optional embodiment of the first aspect, a method is disclosed wherein the single domain particles advantageously are monodisperse. In a further embodiment, the single domain particles may be super-paramagnetic. The super-paramagnetic particles can be spheric.

In a particular embodiment, a method is disclosed wherein the single domain particles comprise iron oxide. In a particular embodiment, the single domain particles can comprise $Fe_3O_4$ (magnetite). The diameter can be between about 5 nm and 100 nm, e.g. between about 5 nm and 60 nm. In another embodiment, the single domain particles can comprise $Fe_2O_3$. The diameter can be between about 5 nm and 100 nm, e.g. between about 5 nm and 80 nm.

In another embodiment, a method is recited wherein the RF energy is applied as a continuous wave. In a different embodiment, the RF energy is applied as pulses, such as but not limited hereto, ultra wide bandwidth (UWB) pulses. The pulses may be sub-giga UWB pulses. UWB, especially sub-giga UWB pulses, result in advantageous measurement possibilities at low magnetic fields and low frequencies resulting in a better signal penetration into the body or scanned volume.

UWB may be defined in terms of a transmission from an antenna for which the emitted signal bandwidth exceeds the lesser of about 500 MHz or 20% of the center frequency. Accordingly for sub-giga UWB, the central frequency is lower than 1 GHz and signal bandwidth is at least about 20% of the central frequency. A lower limit for the frequency in the UWB pulses that may be used may be about 1 MHz. In one example, the center frequency may be around 300 MHz.

A further inventive aspect relates to a system for gathering information about an object, the object including single domain particles having a diameter in the range of 5 nm to 100 nm, e.g. about 5 to 80 nm, e.g. in a range of 5 nm to 80 nm, the system comprising a first field generator adapted for generating a static magnetic field of less than about 0.1 Tesla, e.g. lower than about 0.1 Tesla, for the object, e.g. a generator for applying such a static magnetic field to the object, a second field generator adapted for generating RF energy for the object at a frequency to generate Electron paramagnetic resonance (EPR) of the single domain particles, e.g. a generator for applying such RF energy to the object so as to generate EPR of the single domain particles, and a detection unit adapted for detecting the EPR of the single domain particles in the form of an image of the object, e.g. a volumetric image of the object.

In an embodiment of the second aspect, the single domain particles can have a particle diameter between about 5 nm and 100 nm, e.g. between about 5 nm and 60 nm, between about 10 and 30 nm, between about 40 and 60 nm. In an embodiment of the second aspect, a system is disclosed wherein the single domain particles are monodisperse. In a further embodiment, the single domain particles may be super-paramagnetic. The super-paramagnetic particles can be spheric.

In a particular embodiment, a system is disclosed wherein the single domain particles comprise iron oxide. In a particular embodiment, the single domain particles can comprise $Fe_3O_4$ or magnetite. The diameter can be between about 5 nm and 100 nm, e.g. between about 5 nm and 60 nm.

In another embodiment, a system is recited wherein the RF energy is applied as a continuous wave. In a further embodiment, the RF energy is applied as pulses such as, but not limited hereto, UWB pulses.

In another embodiment, a system as recited in any of the previous embodiment is disclosed wherein the RF frequency is below about 1 GHz.

In another embodiment, a system as recited in any of the previous embodiments is disclosed wherein the static magnetic field is below about 0.05 Tesla or below about 0.01 Tesla.

Another inventive aspect relates to a method of gathering information about an object, the object including single domain particles having a predetermined saturation magnetization or a predetermined longitudinal relaxation time, the method comprising selecting an object including single domain particles, applying to the object to a static magnetic field of less than about 0.1 Tesla, e.g. lower than about 0.1 Tesla, applying a RF energy to the object at a frequency to generate electron paramagnetic resonance (EPR) of the single domain particles, and detecting the EPR of the single domain particles. Another inventive aspect also relates to a method for gathering information about an object, the object including single domain particles having a predetermined saturation magnetization or a predetermined relaxation time, the method comprising detecting electron paramagnetic resonance (EPR) of the single domain particles upon interaction of the object with a static magnetic field of less than about 0.1 Tesla and with RF energy at a frequency to generate EPR of the single domain particles. Although interaction of the object with the magnetic field or the RF energy may not be part of the method, the method may comprise applying to the object a static magnetic field of less than about 0.1 Tesla and the method also may comprise applying an RF energy to the object at a frequency to generate Electron Paramagnetic Resonance of the single domain particles.

Such detecting may in some embodiments comprise imaging the EPR of the single domain particles, and in some embodiments imaging in the form of a volumetric image of the object, wherein the object including single domain particles is selected such that the single domain particle show an Electron paramagnetic resonance (EPR) at a magnetic field where substantial no saturation of the magnetization of the single domain particles occurs. In an embodiment of the third aspect, selecting the object includes selecting a single domain particle with a predetermined diameter. Further, in another embodiment, the chemical composition of the particle is selected.

In another embodiment, a method is disclosed wherein maximum about 95% of the saturation magnetization of the single particle domain is obtained. In another embodiment, maximum about 90%, 80%, 70%, 60%, 50%, 40%, 30%, 20%, 10% of the saturation magnetization of the single domain particle is obtained. In an advantageous embodiment, a method is disclosed wherein at least about 95% of the saturation magnetization of the single particle domain is obtained. In other advantageous embodiments, at least about 90%, at least about 80%, at least about 70%, at least about 60%, at least about 50%, at least about 40%, at least about 30%, at least about 20%, at least about 10% of the saturation magnetization of the single domain particle is obtained.

In one advantageous embodiment, a method is disclosed wherein imaging can be obtained for single domain particles having a magnetization as small as about 80% or as small as about 60% or as small as about 40% or as small as about 20% of the saturation magnetization.

In a further embodiment, the single domain particles may be super-paramagnetic. The super-paramagnetic particles can be spheric.

In a further embodiment, selecting the object includes selecting a single domain particle with a predetermined diameter in the range of about 5 nm to 100 nm, e.g. in the range 5 nm to 100 nm, about 5 nm to 80 nm or about 5 nm to 60 nm.

In a particular embodiment, a method is disclosed wherein the single domain particles comprise iron oxide. In a particular embodiment, the single domain particles can comprise $Fe_3O_4$ (magnetite). The diameter can be between 5 nm and 100 nm, e.g. between about 5 nm and 60 nm. In a particular embodiment, the single domain particles can comprise $Fe_2O_3$. The diameter can be between about 5 nm and 100 nm. In some embodiments, particles may be used having a critical single domain diameter larger than about 80 nm or even larger than about 100 nm, such that particles larger than about 80 nm or even larger than about 100 nm may be used e.g. particles with a size up to about 1 μm may be larger. One example may for example be a $\gamma$-$Fe_2O_3$ particle.

In another embodiment, the static magnetic field is lower than about 0.05 Tesla, e.g. lower than about 0.05 Tesla, or lower than about 0.01 Tesla, e.g. lower than about 0.01 Tesla.

In another embodiment, a method is recited wherein the RF energy is applied as a continuous wave. In a further embodiment, the RF energy is applied as pulses, such as, but not limited hereto UWB pulses.

Another inventive aspect relates to a method of gathering information about an object, the object including single domain particles having a predetermined diameter and predetermined saturation magnetization or a predetermined longitudinal relaxation time, the method comprising selecting an object including single domain particles, applying to the object to a static magnetic field of less than about 0.1 Tesla, e.g. less than 0.1 Tesla, applying a RF energy to the object at a frequency to generate electron paramagnetic resonance (EPR) of the single domain nanoparticles, and detecting the EPR of the super-paramagnetic particles. Another inventive aspect also relates to a method for gathering information about an object, single domain particles having a predetermined diameter and predetermined saturation magnetization or a predetermined longitudinal relaxation time, the method comprising detecting Electron paramagnetic resonance (EPR) of the single domain particles upon interaction of the object with a static magnetic field of less than about 0.1 Tesla and with RF energy at a frequency to generate EPR of the single domain particles. Although interaction of the magnetic field or the RF energy with the object may not be part of the method, the method may comprise applying to the object a static magnetic field of less than about 0.1 Tesla and the method also may comprise applying an RF energy to the object at a frequency to generate Electron Paramagnetic Resonance of the single domain particles. Such detecting may in some embodiments comprise imaging the EPR of the single domain particles, and in some embodiments imaging in the form of a volumetric image of the object, wherein the object including single domain particles is selected such that the single domain particle shows magnetization which is at least about 10% of the saturation magnetization, e.g. at least about 10% of the saturation magnetization. In a particular embodiment, the single domain particle shows a magnetization of the particle which is at least about 10%, at least about 20%, at least about 30%, at least about 50%, at least about 80%, at least about 90% of the saturation magnetization.

Any of the additional features can be combined together and combined with any of the aspects. Furthermore, particular and/or advantageous aspects of the invention also are set out in the accompanying independent and dependent claims. Features from the dependent claims may be combined with features of the independent claims and with features of other dependent claims as appropriate and not merely as explicitly set out in the claims. Other advantages will be apparent to those skilled in the art, especially over other prior art. Numerous variations and modifications can be made without departing from the scope of the embodiments described. Therefore, it should be clearly understood that the form of this description is illustrative only and is not intended to limit the scope of the present invention.

DETAILED DESCRIPTION OF CERTAIN ILLUSTRATIVE EMBODIMENTS

Figure 1:
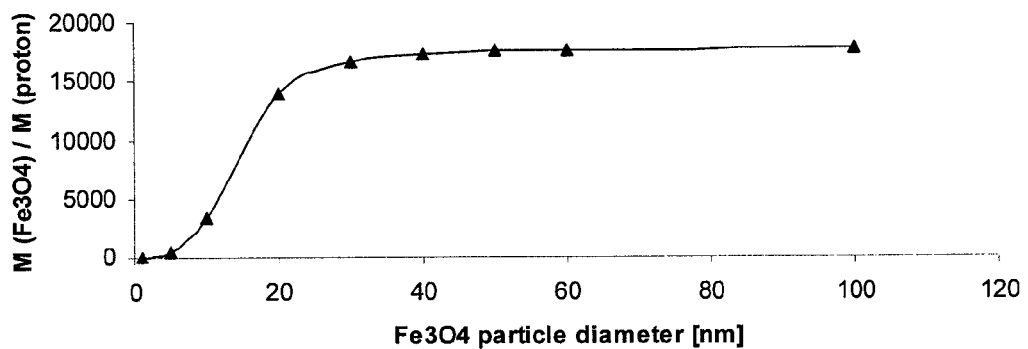
FIG. 1 shows a graph of magnetization of $Fe_3O_4$ nanoparticles at about 100 Gauss as a function of particle diameter compared to the magnetization of protons at about 3 Tesla.

The present invention will be described with respect to particular embodiments and with reference to certain drawings but the invention is not limited thereto. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising" should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Where in embodiments of the present application the term nanoparticles is used, reference is made to particles having a critical dimension, e.g. diameter, in the range of 1 nm to 1000 nm. For a number of embodiments, the size of the particles is further specified to be in a range as provided.

Certain embodiments make use of the magnetization of single domain particles. A definition of single domain particles can be found on http://www.irm.umn.edu/hg2m/hg2m_d/hg2m_d.html.

Single domain particles are defined as particles having a maximum coercivity for a given material occurring within its single domain range. Having larger grain sizes, coercivity decreases as the grain subdivides into domains. For smaller grain sizes, coercivity again decreases, but this time due to the randomizing effects of thermal energy. The critical size for single domain behavior depends on several factors including, the saturation magnetization and the shape of the grain.

In single domain particles, the local magnetization is saturated but not necessarily parallel. Domains are larger than atomic distances and typically between 1 and 100 nanometer.

Super-paramagnetic particles are a specific class of single domain particles. As the particle size continues to decrease within the single domain range, the remanence and coercivity go to zero. When this happens, the grain becomes super-paramagnetic.

A single particle of volume v has a uniform magnetization directed along the easy axis of magnetization. If v is small enough, or the temperature is high enough, thermal energy (kT) will be sufficient to overcome the anisotropy energy separating the (+) and (−) magnetization states and cause a spontaneous reversal of magnetization. The single particles may be particles having a sufficiently long longitudinal relaxation time, e.g. a relaxation time longer than the death time of the detection unit. The measured signal of such single domain resonant particles is proportional to the magnetization. Therefore, it is beneficial to use particles made of a compound that show an electron paramagnetic resonance (EPR) with a magnetization being as large as possible, advantageously as large as the saturation magnetization. The latter may allow to obtain the maximal amplitude of the measured signal. The diameter could be selected such that a maximum alignment of all particles at a low static magnetic field is possible. A small static magnetic field implies a low resonant frequency and therefore a higher penetration depth of the RF field and decreasing heat dissipation into the human body or small animal.

$$\vec{M}(\vec{r}, t) = M_0(\vec{r}) \left[ \coth\left(\frac{m|\vec{B}(\vec{r}, t)|}{k_B T}\right) - \frac{k_B T}{m|\vec{B}(\vec{r}, t)|} \right] \vec{e}_{\vec{B}}(\vec{r}, t) \quad \text{(eq. 1)}$$

Figure 2:
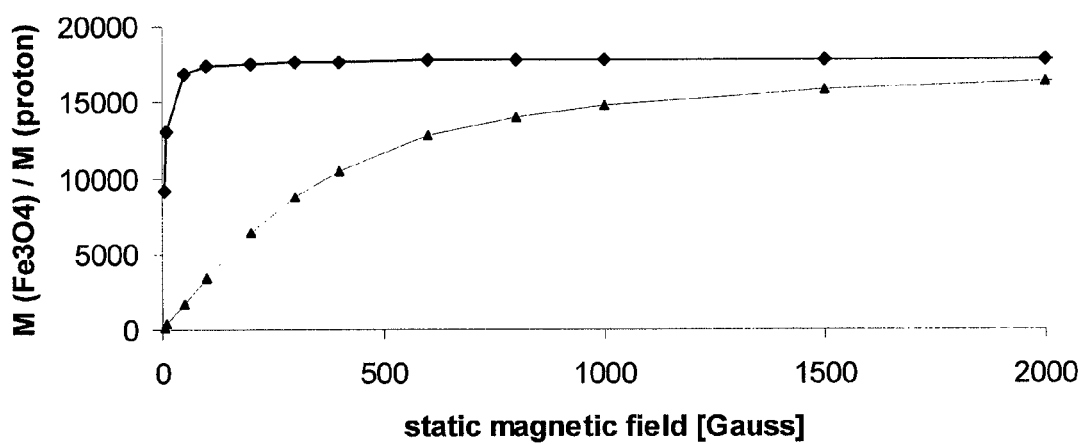
FIG. 2 shows a graph of magnetization of $Fe_3O_4$ particles of 10 nm (triangles) and 40 nm (diamonds) as a function of the static magnetic field compared to the magnetization of protons at about 3 T.

The Langevin theory of paramagnetism (eq. 1) gives the total magnetization as a function of the static magnetic field, the diameter of the particles, the number of the particles contained in a unit volume, the saturation magnetization of the compound and the temperature. Simulations based on the Langevin theory allow comparison of the magnetization of Fe3O4 super paramagnetic particles, e.g. super paramagnetic nanoparticles, with the magnetization of protons responsible for the echo signal in traditional MRI. The magnetization of about 40-60 nm iron oxide particles is about 17000 times higher than the magnetization of protons at 3 Tesla at room temperature. FIG. 1 illustrates the magnetization as function of the particle diameter, relative to the magnetization of protons at 3 Tesla at room temperature. For the same particle diameter the total alignment of the electron spins is achieved at about 50 Gauss with a longitudinal relaxation time of at least 10 ns, advantageously at least 20 ns. FIG. 2 indicates the magnetization as function of static magnetic field, and illustrates for particles with a size of about 10 nm (diamonds) and particles with a size of about 40 nm (triangles) at which static magnetic field saturation is obtained.

In certain embodiments of the present invention, methods and systems are provided for gathering information about an object that includes single domain particles having a diameter in the range of about 5 nm to 80 nm, e.g. in the range from 5 nm to 80 nm. In certain embodiments of the present invention, the system comprises a first field generator adapted for generating a static magnetic field of less than about 0.1 Tesla for the object, a second field generator adapted for generating an RF energy for the object at a frequency to generate electron paramagnetic resonance (EPR) of the single domain particles, and a detection unit adapted for detecting the electron paramagnetic resonance of the single domain particles. Such a detection unit may be a mere detection of presence of such particles, which can be referred to as single pixel imaging indicating presence or non presence of such particles. The detection unit may be adapted for detecting the electron paramagnetic resonance of the single domain particles in the form of an image. The image may be single pixel or multi-pixel. In advantageous embodiments, the detection using may be adapted for detecting the electron paramagnetic resonance of the single domain particles in the form of a volumetric image of the object. Such volumetric image may be a two-dimensional or three-dimensional image. The system also may be referred to as an imaging system. Similarly, the corresponding method comprises the steps of generating a static magnetic field of less than about 0.1 Tesla for the object, e.g. applied to the object, the step of generating an RF energy for the object at a frequency to generate electron paramagnetic resonance (EPR) of the single domain particles in the object, and the step of detecting the electron paramagnetic resonance of the single domain particles in the form of a volumetric image of the object. Such a method also may be referred to as an imaging method. Further features and advantages, standard or optional to embodiments of the present invention are by way of illustration further described below in exemplary embodiments.

Figure 3:
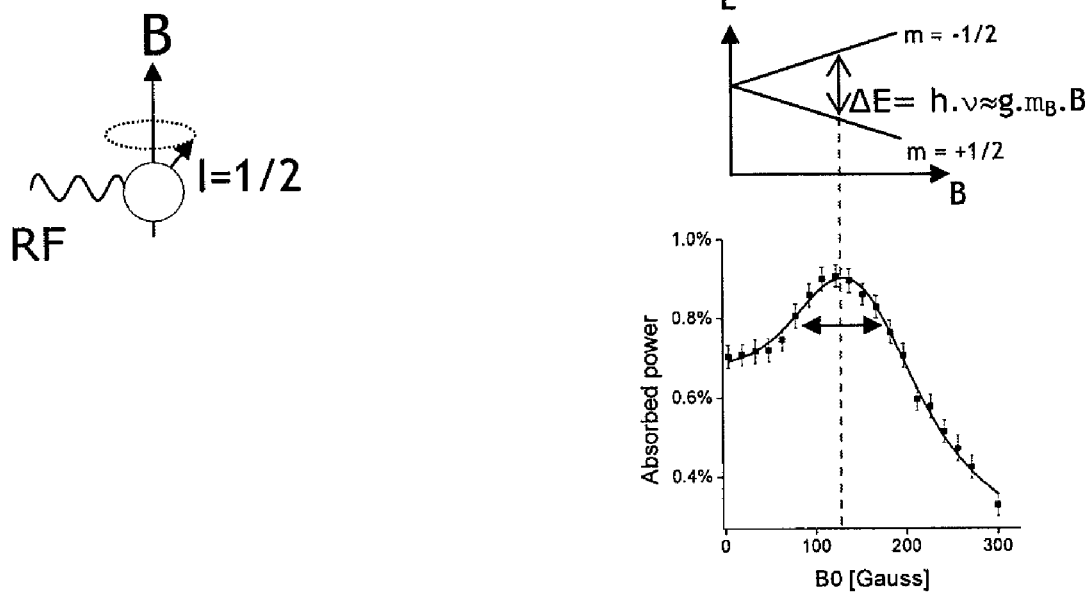
FIG. 3: shows a graph of EPR in continuous wave on $Fe_3O_4$ nanoparticles.

In certain embodiments of the present invention, the methods and apparatus can allow for Electron paramagnetic resonance (EPR) of single domain nanoparticles in continuous wave. Single domain particles may be in the range 5 nm to 100 nm are preferably in the range of about 5-80 nm, e.g. the diameter of the particles may be in the range of about 5 nm to 80 nm. In some embodiments the diameter of the particles may be in the range of about 10 nm to 30 nm or in the range of about 40 nm to 60 nm. The single domain particle can be super-paramagnetic. The particles are preferably single domain particles such as single domain magnetite Fe3O4 particles. Another example of a single domain particle is hematite which may be superparamagnetic or not. An further example of a single domain particle is maghemite. The particles are preferably spheric, monodisperse and with a crystal structure allowing a high saturation magnetization. The electron spin of a paramagnet embedded in a static magnetic field B, will align parallel with the direction of this field and will process around the field with a specific frequency ν, the Larmor frequency. The static field applied in accordance with this embodiment of the present invention can be about 0.1 Tesla or less, for example 0.1 Tesla or less, or about 0.01 Tesla or less, for example 0.01 Tesla or less. When a continuous RF-field is applied to the paramagnet particles and the frequency of this RF-field is equal to the Larmor frequency, the resonance conditions are fulfilled and the direction of the spins will flip to the anti-parallel state and back. The population of the energy states of the electron spins will mix causing the absorption of the power of the RF-field (FIG. 3). The magnetic resonance of these particles can be detected based on techniques well known in MRI imaging In particular an apparatus with coaxial body coil (gradient and RF coils) and magnetic windings (e.g. with an outer cryoshield) may be used to apply the continuous static and RF fields for this embodiment. The selection of the particle size may be a trade off between an attempt for obtaining a magnetization as close as possible to the saturation magnetization for a low magnetic field and sufficiently long enough longitudinal relaxation time on the one hand for which a larger particle size would be selected, and a significant small particle on the other hand for having a significant narrow and high amplitude resonant signal.

Figure 4:
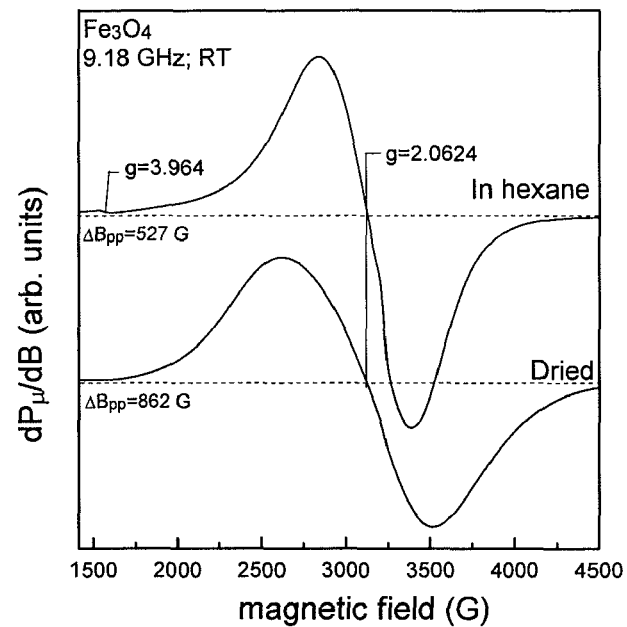
FIG. 4 is a graph showing the first derivative of the EPR resonance of $Fe_3O_4$ nanoparticles of about 10 nm and on $Fe_2O_3$ nanoparticles of about 60 nm.
Figure 4:
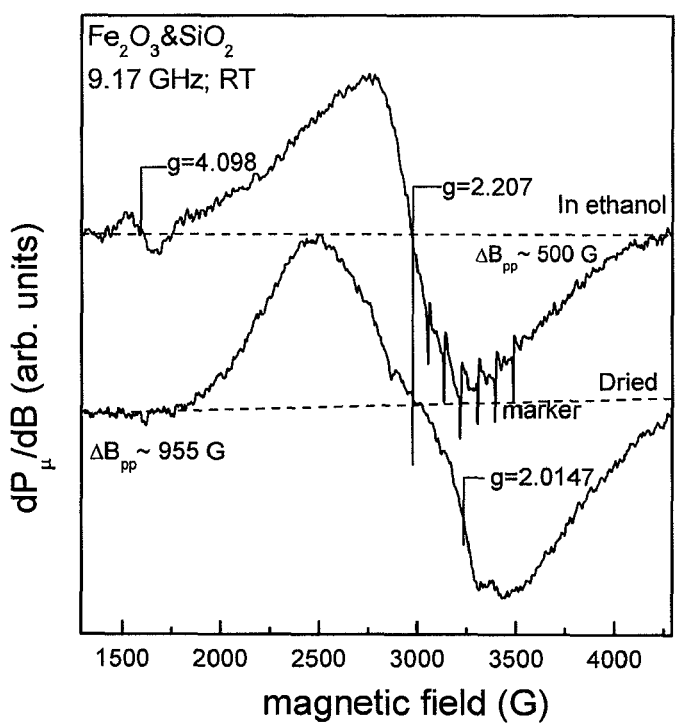

From electron paramagnetic resonance (EPR) experiments in continuous wave the g-factor of g=2.0624 for Fe3O4 and g=2.207 for Fe2O3 has been obtained (FIG. 4). Both measurements where performed with an RF frequency of 9.18 GHz and high magnetic fields of around 3000 Gauss in order to saturate the magnetization. The measurement confirmed that Fe3O4 has a larger saturation magnetization (MS=480 kA/m) compared to γ-Fe2O3 (MS=380 kA/m) and α-Fe2O3 (MS=2.5 kA/m). The resonance of Fe2O3 is broader than the one of Fe3O4.

Figure 5:
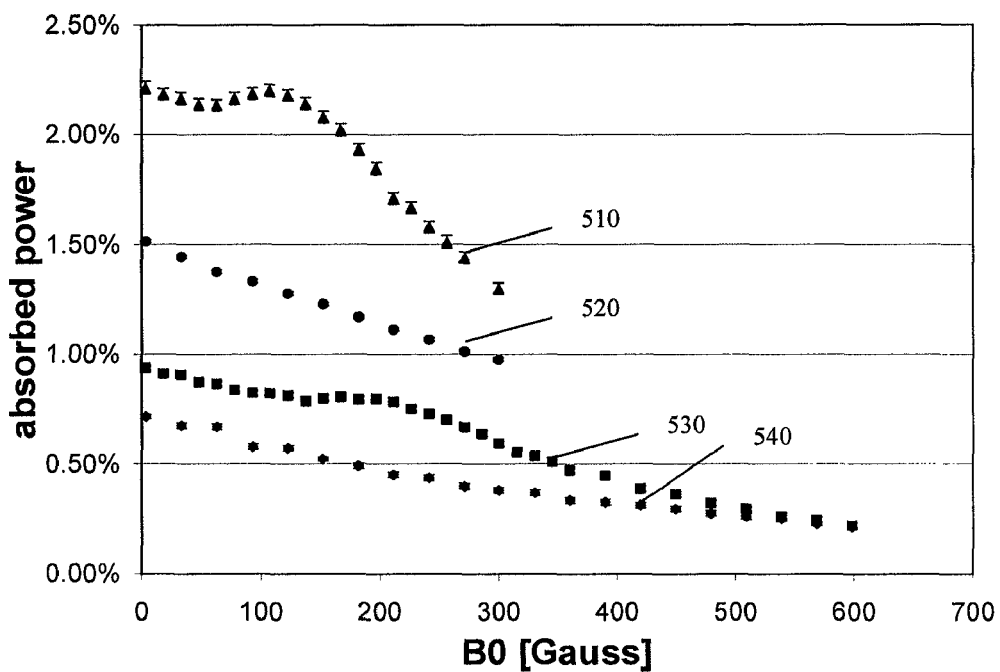
FIG. 5 is a graph (top to bottom) of EPR on $Fe_3O_4$ nanoparticles of about 10 nm in Hexane at low magnetic fields at $\nu$=740 MHz, of the corresponding background signal at $\nu$=740 MHz, of EPR on $Fe_3O_4$ nanoparticles of about 10 nm at low magnetic fields at ν=480 MHz and of the corresponding background signal at ν=480 MHz.

EPR experiments at low frequencies of about 480 MHz and 740 MHz were performed demonstrating the non-specific absorption of the RF-field (FIG. 5). Data 510 show Fe3O4-particles recorded at 480 MHz, data 520 show a corresponding background, data 530 show Fe3O4-particles recorded at 740 MHz, and data 540 show a corresponding background. Above 600 Gauss the magnetization of 10 nm Fe3O4-particles is saturated, all electron spins are aligned with the static magnetic field and the sample becomes transparent for the RF-field. Embodiments of the present invention make use of low frequencies in the range below about 1 GHz.

The non-specific absorption can be understood by the Langevin theory. At very low fields, before the magnetization is saturated, not all electron spins are aligned with the static magnetic field. When an RF-field is imposed on the ensemble, the fraction of the electron spins that is not aligned with the static magnetic field will rotate with the RF-field resulting in the absorption of the RF-power. The higher the magnetic field, the lower this fraction and the lower the non-specific absorption. On top of this non-specific absorption, the resonant absorption is caused by the fraction of the ensemble that is aligned with the static magnetic field. This fraction will absorb the RF-power only under resonance conditions resulting in a Gaussian shape on top of the decreasing non-specific absorption.

Figure 6A:
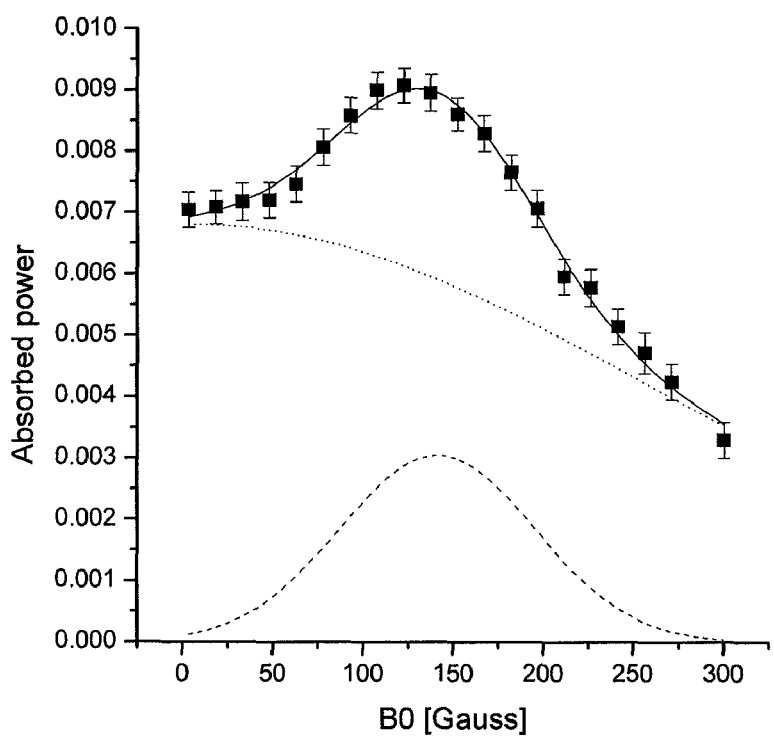
FIG. 6A to FIG. 6D illustrate non specific absorption for $Fe_3O_4$ with about 10 nm at 480 MHz (FIG. 6A) and at 740 MHz (~1 mg $Fe_3O_4$/ml) (FIG. 6B), and non specific absorption for Resovist® with a $Fe_3O_4$ core of 5 nm at 480 MHz (38.6 mg $Fe_3O_4$/ml) (FIG. 6C), and non specific absorption for SiMAG/T-basic particles from Chemicell with γ-$Fe_2O_3$ cores of 10-20 nm in a polymer matrix 500 nm at 480 MHz (80 mg particles/ml) (FIG. 6D).
Figure 6B:
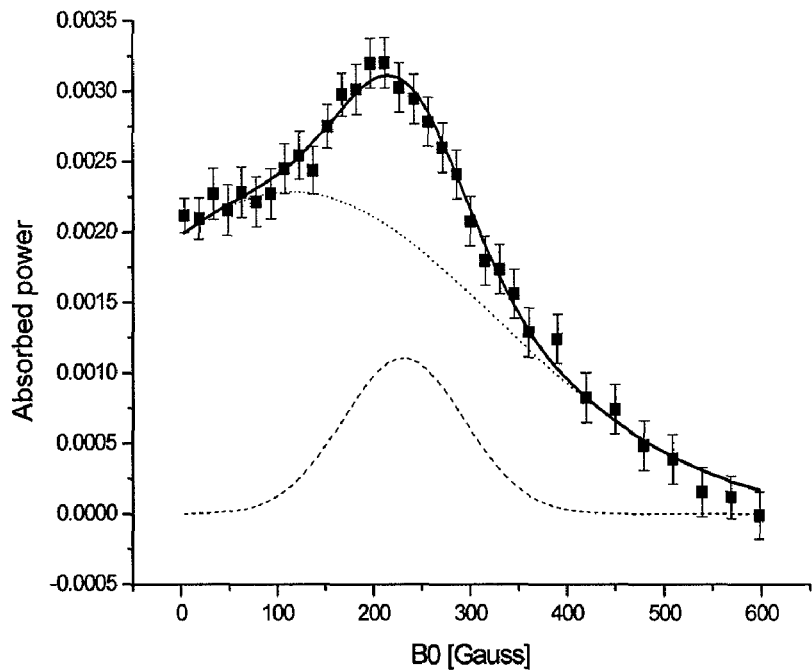
Figure 6C:
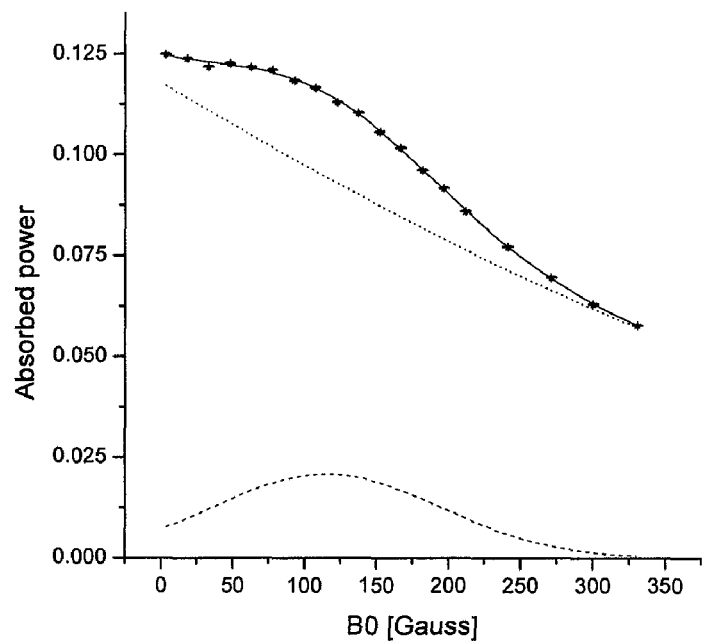
Figure 6D:
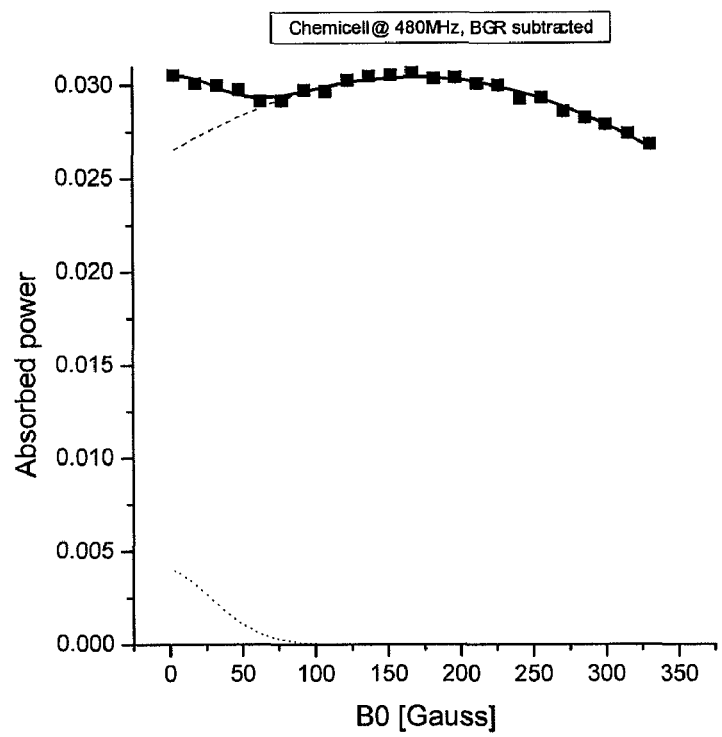

The EPR experiments on Fe3O4 with different diameters and on γ-Fe2O3 demonstrate the typical behavior of the non-specific absorption (FIG. 6A to FIG. 6D). FIG. 6A and FIG. 6B illustrate the absorbed power spectra and background subtracted power spectra of a Fe3O4 measured at a frequency of 480 MHz, respectively 740 MHz. FIG. 6C illustrates the absorbed power spectra and background subtracted absorbed power spectra of Resovist® particles with a Fe3O4 core of 5 nm measured at a frequency of 480 MHz. FIG. 6D illustrates the absorbed power spectrum and the background subtracted power spectrum of SiMAG/T-basic particles from Chemicell with γ-Fe2O3 cores of 10-20 nm in a polymer matrix 500 nm.

In accordance with other embodiments of the present invention, methods and apparatus can allow EPR on single domain nanoparticles in pulsed mode. When EPR is performed on single domain nanoparticles reaching their maximum saturation magnetization at low fields, the amplitude of the resonance signal will be maximal at this low field and therefore the sensitivity will be maximal at low fields eliminating the need to apply higher static magnetic fields in order to obtain a higher sensitivity as is the case with MRI based on the resonant signal of protons.

The single domain nanoparticles have a very large magnetization compared with the electron spin resonance (ESR) of free radicals or other paramagnets which makes imaging with iron-oxide labels possible.

Accordingly, in a second specific embodiment of the present invention methods and devices are provided that can allow for EPR on single domain nanoparticles with ultra-wide-band (UWB) pulses.

As demonstrated in FIGS. 4, 5 and 6a to 6d with the absorption spectrum of single domain iron oxide nanoparticles, one can conclude that the magnetic resonance of single domain nanoparticles is very broad, broader than about 20% of the central frequency.

Figure 7:
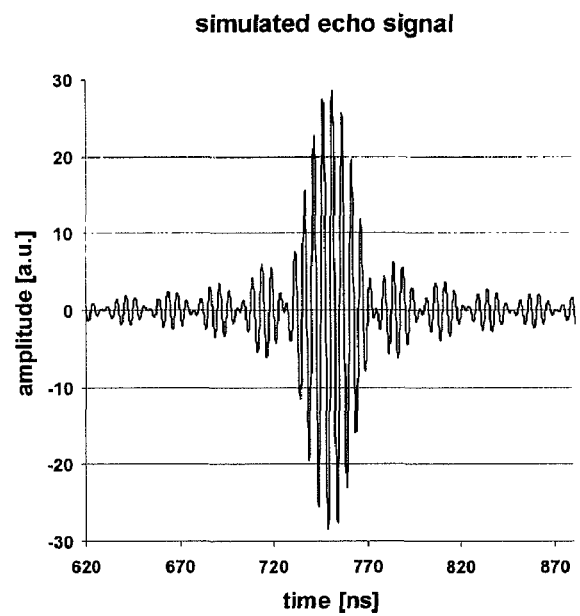
FIG. 7 illustrates UWB pulses applied on a paramagnetic nano-label.

When an ultra wideband pulse, containing a broadband frequency spectrum, is applied to the nanoparticle paramagnets all or a selection of the electron spins of the ensemble will be tilted simultaneously over a specific angle $\alpha$ with respect to the static magnetic field. This will yield the total magnetization of the ensemble in the direction $\alpha$. In the most favorable case, an ultra wideband RF-pulse or pulse sequence will flip the spins until they are perpendicularly oriented to the static magnetic field. The magnetic dipole moment of the processing spins, a rotating magnetic field, will induce an RF-field with the maximal amplitude proportional to the magnetization of the ensemble and with the same frequency of the transmitted ultra wideband pulse, which is the echo-signal of the particles (FIG. 7).

Figure 8:
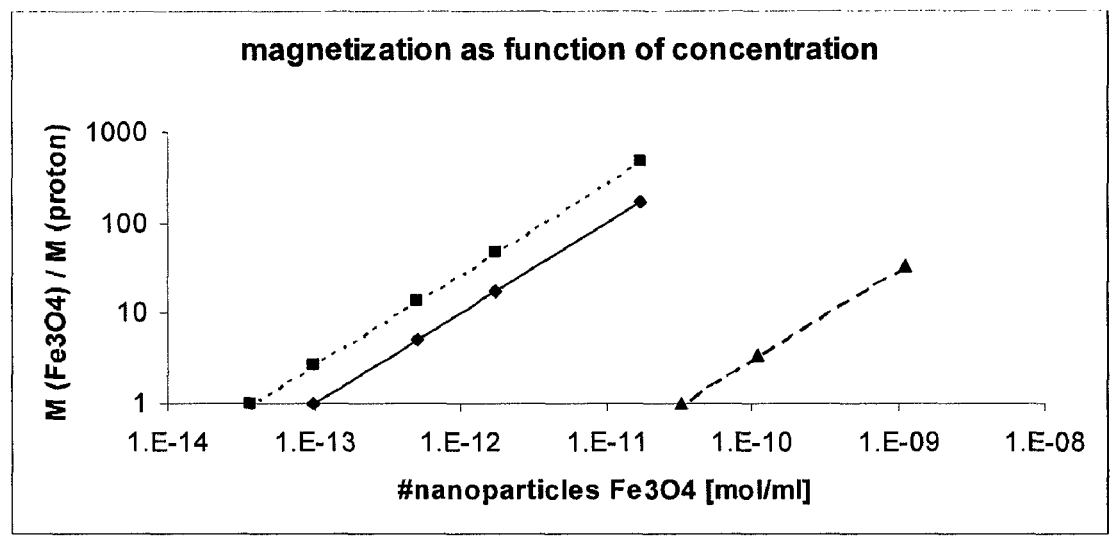
FIG. 8 shows magnetization of $Fe_3O_4$ particles about 10 nm at 100 Gauss (triangle) 40 nm at 100 Gauss (diamonds), 40 nm at 50 Gauss (square) compared to the magnetization of protons at 3 T.

FIG. 8 illustrates the magnetization of Fe3O4 particles of about 10 nm at 100 Gauss (triangle), the magnetization of Fe3O4 particles of about 40 nm at 100 Gauss (diamonds) and the magnetization of Fe3O4 particles of about 40 nm at 50 Gauss (square) compared to the magnetization of protons at 3 T, i.e. compared to traditional MRI. In order to estimate the sensitivity of the UWB-MRI technology compared to traditional MRI, one should also take the signal to noise ratio into account of the broadband pick-up antennas, SNR~$\Delta v^* v$. Again, a small static magnetic field implies a low resonant frequency and therefore a lower SNR ratio.

When sending a broadband signal through a coil antenna, one should take the characteristic transfer function into account. The broadband signal will be deformed by the coil itself. Typically the power at the side of the power spectrum will be attenuated while a flat power spectrum in frequency domain is advantageous to bring the total ensemble of electron spins or a selection thereof simultaneously in resonance. The input signal of the antenna may be shaped to compensate the power loss due to reflections and mismatch of the antenna at the side wings of the spectrum.

Localization and imaging of the particles may for example be obtained by the echo signal under different resonance conditions e.g. variation of the static magnetic field with a field gradient. Also localization may for example be obtained using an UWB-radar. Localization may be obtained when a Radon Transform is performed. In another example, localization may be performed by the combination of the three techniques mentioned.

Identification of the nanoparticles may be performed by the resonant signature of the labels.

Activation of the nanoparticles is possible by applying a continuous RF-field, or by applying a sequence of the RF-pulses.

According to an embodiment employing pulsed RF energy generation, improved apparatus or methods for detection using UWB are provided, as well receivers for such systems, and/or corresponding methods and software for carrying out the methods, and/or methods of using UWB pulses to activate tags and/or tags for such apparatus and methods.

For example a detection system is provided comprising a transmitter for transmitting a series of pulses of UWB electromagnetic radiation, at least one receiver for identifying echo pulses of the series of pulses and being adapted to identify a signature imposed on the echo pulses, further comprising single domain particles having a diameter of between about 5 and 50 nm, the signature being indicative of the single domain particles having a diameter between about 5 and 50 nm exhibiting magnetic resonance induced by the series of pulses.

Another aspect of this embodiment is a receiver for receiving echoes of a series of pulses of UWB electromagnetic radiation, comprising: means to identify a signature imposed on the echo pulses, the signature being indicative of reflection from single domain particles having a diameter of between about 5 and 50 nm exhibiting magnetic resonance induced by the series of pulses.

Another aspect is the receiver having a correlator circuit for identifying echo pulses from the series of pulses and also for identifying the signature.

Another aspect is a receiver for detecting single domain particles having a diameter of between about 5 and 50 nm having a magnetic resonance response to illumination by pulses of UWB electromagnetic radiation, the receiver having: a detector for detecting the pulses after they have interacted with the single domain particles having a diameter of between about 5 and 50 nm, and a discriminator arranged to identify in the detected pulses the magnetic resonance response of the single domain particles having a diameter of between about 5 and 50 nm.

Another aspect provides a method of scanning an item tagged with a tag having a material having a magnetic resonant response, the method includes illuminating the item with pulses of UWB electromagnetic radiation, detecting the pulses after they have interacted with single domain particles having a diameter of between about 5 and 50 nm, and identifying in the detected pulses the magnetic resonance response of the single domain particles having a diameter of between about 5 and 50 nm. Such a method may employ a method for obtaining information of an object.

Another aspect provides a method of activating a tag in an item, the tag having single domain particles having a diameter of between about 5 and 50 nm and having a magnetic resonant response, the method includes illuminating the item with pulses of UWB electromagnetic radiation or by applying continuous wave electromagnetic radiation, such that the magnetic resonance response of the tag causes activation of the tag. It is an advantage of an embodiment using pulsed RF energy that it allows controlling heat dissipation by the activation. Activation can include cellular targeting. Other examples of activation are hyperthermia and thermoablation.

Another aspect provides a tag for use by the system, receiver or method, the tag having single domain particles having a diameter of between 5 nm and 80 nm, e.g. between about 5 and 50 nm, exhibiting a magnetic resonance response arranged to provide an identifiable magnetic resonance signature response to illumination by pulses of UWB radiation or by continuous wave electromagnetic radiation, such that different tags can be identified and distinguished by their signatures. Examples of tags that may be used are MRI contrast agents such as Resovist® (Schering) and Endorem® (Guerbet), iron-oxide cores with an average diameter of 5 nm and a Carbotran (Ø 60 nm) and Dextran (Ø 80-150 nm) coating respectively. Other examples are Ocean nanotech iron oxide nanoparticles (www.oceannanotech.com) or reade iron oxide nanoparticles (www.reade.com). In some examples, an iron oxide core may be used allowing to make the particles suitable as paramagnetic labels, while the coating of these particles must be adapted in order to selectively bind with the biomolecules of interest.

By way of illustration, the present invention not being limited thereto, an example of the use of EPR detection and/or imaging using single domain particles is given below.

In one example, the nanoparticles act as a label to visualize biological processes within the body of a creature, e.g. an animal or human body. The visualization may be for processes within the body of a living creature. Nevertheless, the present invention is not limited thereto. Before administration, the nanoparticles can be coated (e.g. with dextran), to make them biocompatible, e.g. if this is not yet the case. The size of the particle and the coating will determine the final biodistribution within the animal or human body. The particles accumulate in a specific tissue or body fluid, and can be monitored by visualization of the labels (e.g. perfusion test, liver monitoring).

In addition, specific functional groups on top of the coating will allow a specific binding with a biomolecule of interest (e.g. antibody/antigen) or pharmaceutical product. According to a particular example, probes may be provided on the surface so as to bind to a specific target of interest. Probes used for finding particular targets also may include a strand of oligonucleotides, DNA, RNA or PNA (partially), atoms, molecules, functional groups, antibodies, antigens, etc. In one application, such a specific binding can take place before administration. In this case, the nanoparticle will act as a label in order to track a product within the body.

Alternatively, the specific binding can take place after administration within the body, in order to detect the presence of a biomolecule in a specific tissue or body fluid of the body.

In one example, detection of the presence, which could also be referred to as single pixel imaging can be performed. A bound nanoparticle-label, accumulates at a specific site. An in-vivo detector may be used for detection via the label of the presence of a specific tissue or body fluid, such as e.g. metastases. The in-vivo detector also may detect, via the label, the absence of a specific tissue or body fluid. One particular example application may be testing whether malicious cells have been removed, e.g. during surgery.

In another example, detection of presence may be performed for checking binding of labels to biomolecules In a further example, multiple pixel imaging is performed, e.g. in-vivo imaging for functional or molecular imaging, diagnostics and therapy monitoring. Via labeling, biological processes, tissues and bodily fluids can be monitored. Particular examples of applications may be detecting or following tumor growth, checking the presence of antibodies, etc.

For in-vivo detection or imaging, the system for characterization advantageously may be compact, such that it can be used as a handheld device.

Figure 9:
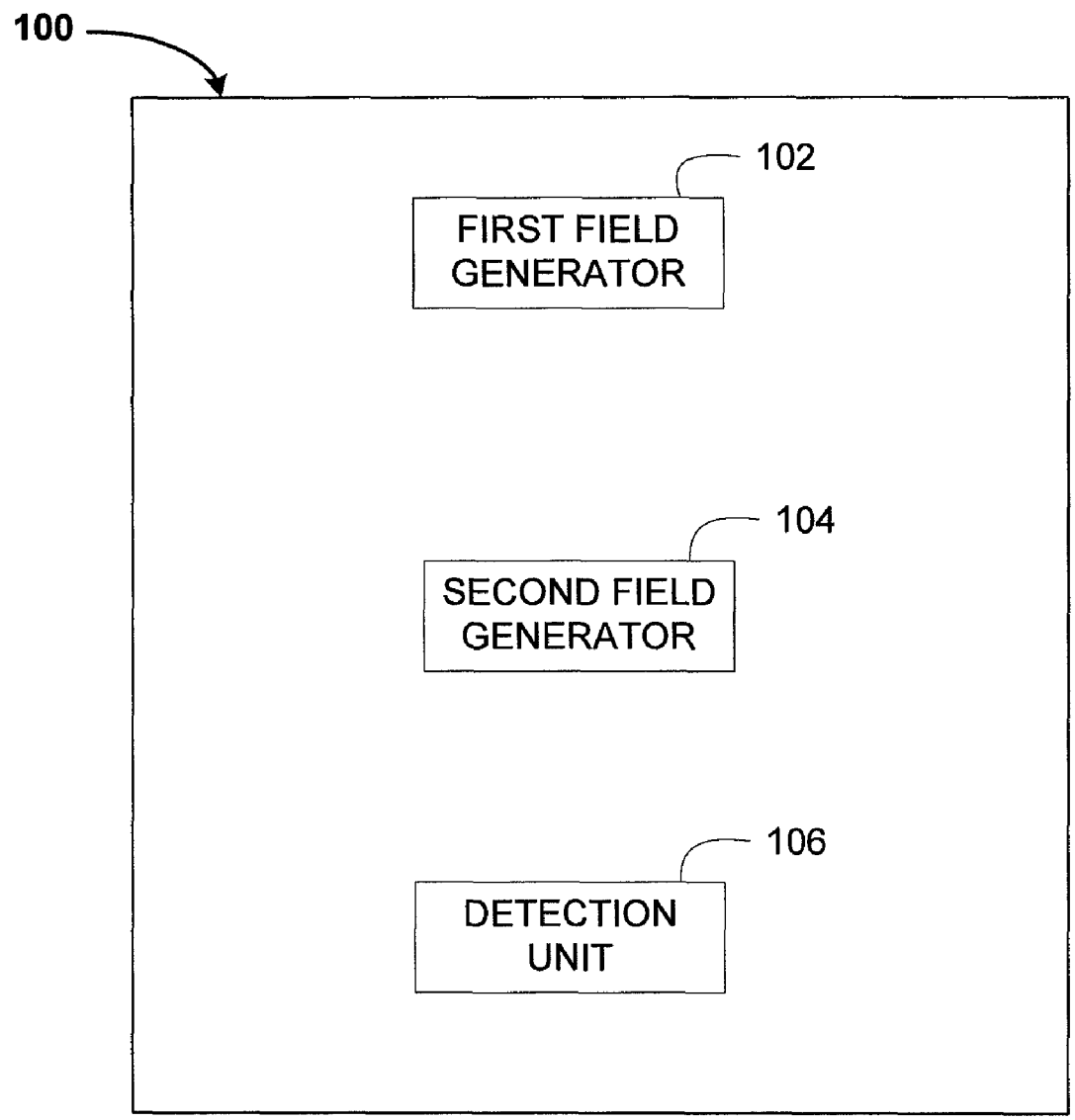
FIG. 9 shows a block diagram illustrating one embodiment of a system for gathering information about an object.

FIG. 9 shows a block diagram illustrating one embodiment of a system for gathering information about an object. The object comprises single domain iron oxide particles having a diameter in the range of about 5 nm to 80 nm. The system 100 comprises a first field generator 102 configured to generate a static magnetic field of less than about 0.1 Tesla for the object. The system 100 may further comprise a second field generator 104 configured to generate an RF energy for the object at a frequency to generate electron paramagnetic resonance (EPR) of the single domain iron oxide particles. The system 100 may further comprise a detection unit configured to detect the electron paramagnetic resonance of the single domain iron oxide particles in the form of an image of the object.

Figure 10:
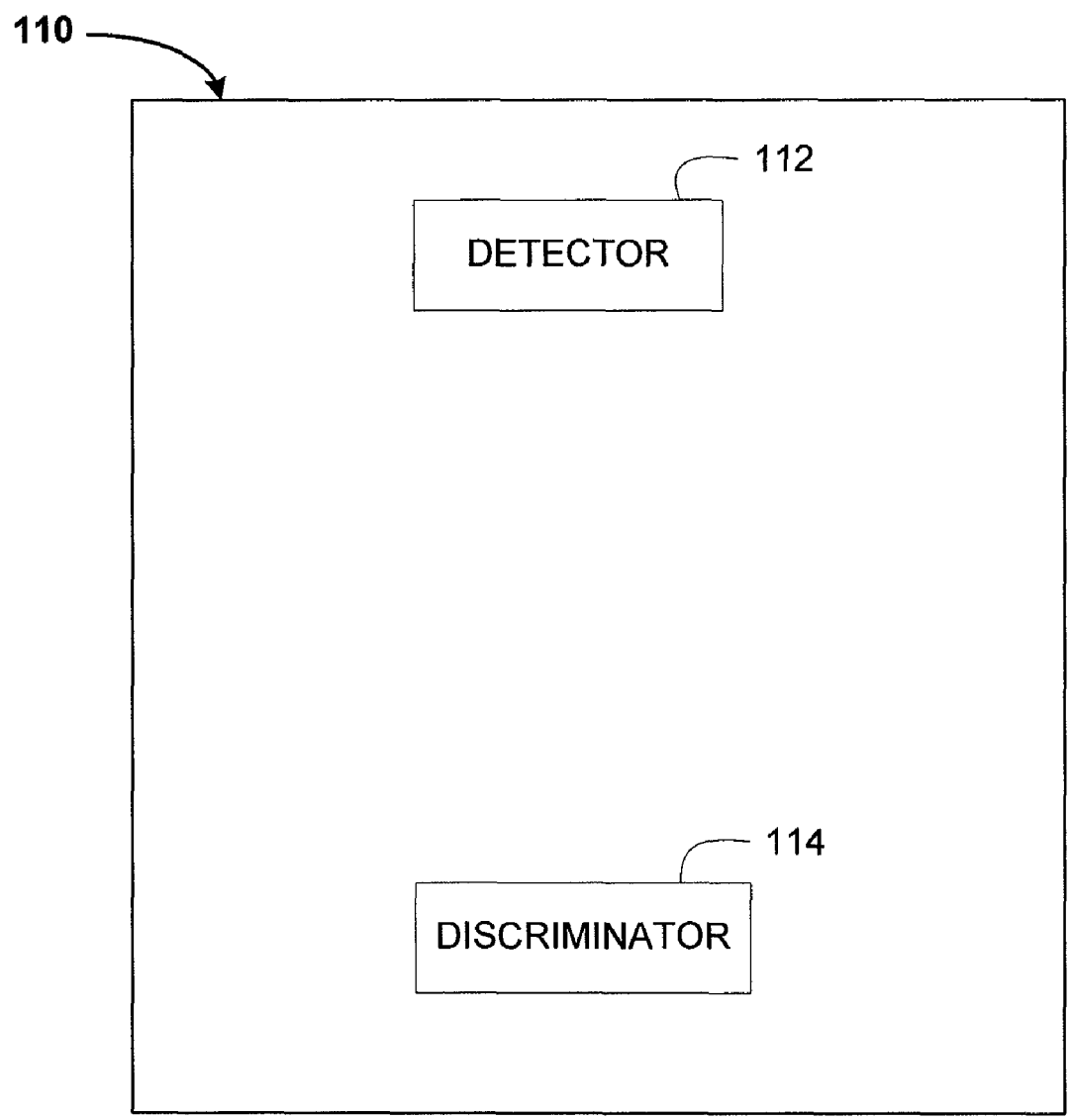
FIG. 10 shows a block diagram illustrating one embodiment of a receiver for detecting single domain particles comprising iron oxide.

FIG. 10 shows a block diagram illustrating one embodiment of a receiver for detecting single domain particles comprising iron oxide. The single domain particles have a diameter in the range of about 5 nm to 80 nm and have an electron paramagnetic response to an applied static magnetic field of less than about 0.1 Tesla for the object and an applied RF energy. The receiver 110 comprises a detector 112 configured to detect a response of the single domain particles comprising iron oxide in reply to the applied RF energy, the detecting being detecting in the form of an image. The receiver 110 may further comprise a discriminator 114 configured to identify in the detected response the electron paramagnetic response of the single domain particles.

Although systems as disclosed are embodied in the form of various discrete functional blocks, they could equally well be embodied in an arrangement in which the functions of any one or more of those blocks or indeed, all of the functions thereof, are realized, for example, by one or more appropriately programmed processors or devices.

In one aspect, embodiments of the present invention also relate to computer-implemented methods for performing at least part of the methods for directly imaging using a resonance technique or for gathering information about an object or for identifying or activating a tag as described above or to corresponding computing program products. Such methods may be implemented in a computing system, such as for example a general purpose computer. The computing system may comprise an input means for receiving data. The system may be or comprise a data processor for processing data, e.g. the electron paramagnetic resonance data of the single domain particles. The computing system may include a processor, a memory system including for example ROM or RAM, an output system such as for example a CD-rom or DVD drive or means for outputting information over a network. Conventional computer components such as for example a keyboard, display, pointing device, input and output ports, etc also may be included. Data transport may be provided based on data busses. The memory of the computing system may comprise a set of instructions, which, when implemented on the computing system, result in implementation of part or all of the standard steps of the methods as set out above and optionally of the optional steps as set out above. Therefore, a computing system including instructions for implementing part or all of a method for directly imaging using a resonance technique or for gathering information about an object or for identifying or activating a tag processing correspondingly obtained information is not part of the prior art.

Further aspect of embodiments of the present invention encompass computer program products embodied in a carrier medium carrying machine readable code for execution on a computing device, the computer program products as such as well as the data carrier such as DVD or CD-rom or memory device. Aspects of embodiments furthermore encompass the transmitting of a computer program product over a network, such as for example a local network or a wide area network, as well as the transmission signals corresponding therewith.

In method embodiments according to the present invention, the interaction between object and magnetic field or RF energy may be not part of the method. Method embodiments according to the present invention may thus encompass only the step of detecting upon interaction.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A system for gathering information about an object, the object comprising single domain iron oxide particles having a diameter in the range of 5 nm to 80 nm, the system comprising:
    a first field generator configured to generate a static magnetic field of less than 0.1 Tesla for the object;
    a second field generator configured to generate an radio frequency (RF) energy as pulses for the object at a frequency to generate electron paramagnetic resonance (EPR) of the single domain iron oxide particles, the second field generator being configured to transmit a series of pulses of electromagnetic radiation; and
    a detection unit configured to detect the electron paramagnetic resonance of the single domain iron oxide particles, the detection unit being configured to identify echo pulses of the transmitted pulses, the echo pulses being generated as the transmitted pulses are reflected by the single domain particles.

2. The system according to claim 1, wherein the detection unit is adapted for detecting the electron paramagnetic resonance of the single domain particles in the form of a volumetric image of the object.

3. The system according to claim 1, wherein the second field generator is adapted for generating the RF energy at an RF frequency below 1 GHz.

4. The system according to claim 1, wherein the first field generator is adapted for generating a static magnetic field of less than 0.05 Tesla.

5. The system according to claim 1, wherein the second field generator is adapted for generating the RF energy as ultra wide band pulses.

6. The system according to claim 1, wherein the detection unit is configured to identify a signature imposed on the echo pulses, the signature being indicative of the electron paramagnetic resonance exhibited by the single domain particles.

7. The system of claim 1, wherein the second field generator transmits the series of pulses to simultaneously tilt all or a fraction of electron spins of the single domain particles, wherein the echo pulses are generated as an induced RF-field with a maximal amplitude proportional to a magnetization of the electron spins.

8. The system of claim 7, wherein the field is induced by a magnetic dipole moment of the electron spins.

9. A method of gathering information about an object, the object comprising single domain particles which comprises iron oxide, the particles having a diameter in the range of 5 nm to 80 nm, the method comprising:
    generating a static magnetic field of less than 0.1 Tesla for the object;
    transmitting pulses of electromagnetic radiation for the object at a frequency to generate electron paramagnetic resonance (EPR) of the single domain particles in the object; and
    detecting electron paramagnetic resonance (EPR) of the single domain particles upon interaction of the object with the static magnetic field and the pulses, the EPR detecting comprising identifying echo pulses of the transmitted pulses, the echo pulses being generated as the transmitted pulses are reflected by the single domain particles.

10. The method according to claim 9, wherein the detecting comprises detecting in the form of a volumetric image of the object.

11. The method according to claim 9, wherein the single domain particles are super-paramagnetic particles.

12. The method according to claim 9, wherein the single domain particles comprise magnetite.

13. The method according to claim 9, wherein generating RF energy comprises generating RF energy at a RF frequency below 1 GHz.

14. The method according to claim 9, wherein generating RF energy comprises generating the RF energy as ultra wide band pulses.

15. The method according to claim 9, wherein detecting the electron paramagnetic resonance comprises identifying a signature imposed on the echo pulses, the signature being indicative of electron paramagnetic resonance exhibited by the single domain particles.

16. The method according to of claim 9, wherein the single domain particles have a predetermined saturation magnetization and the static magnetic field is selected so that a magnetization of the single domain particles of at least 10% of the saturation magnetization is reached.

17. A method of scanning an item tagged with a tag, the method comprising gathering information about the tag by performing a method for gathering information about an object according to claim 9.

18. A non-transitory computer-readable medium having stored therein a program which, when executed on a computer, performs the method according to claim 9.

19. A method of scanning an item tagged with a tag, the tag comprising single domain particles which comprises iron oxide, the particles having a diameter in the range of 5 nm to 80 nm, the method comprising gathering information about the tag by performing a method for gathering information about an object according to claim 9.

20. A method of gathering information about an object, the object comprising single domain particles which comprise iron oxide having at least a predetermined longitudinal relaxation time, the method comprising:
    detecting pulsed electron paramagnetic resonance (EPR) of the single domain particles upon interaction of the object with a static magnetic field of less than 0.1 Tesla and with RF energy transmitted as pulses of electromagnetic radiation for the object at a frequency to generate EPR of the single domain particles, the detecting being detecting in the form of an image of the object, the EPR detecting comprising identifying echo pulses of the transmitted pulses, the echo pulses being generated as the transmitted pulses are reflected by the single domain particles.

21. A receiver for detecting single domain particles comprising iron oxide, the single domain particles having a diameter in the range of 5 nm to 80 nm and having an electron paramagnetic response to an applied static magnetic field of less than 0.1 Tesla for the object and an applied RF energy transmitted as pulses of electromagnetic radiation for the object at a frequency to generate electron paramagnetic resonance (EPR) of the single domain particles, the receiver comprising:

a detector configured to detect a response of the single domain particles comprising iron oxide in reply to the applied RF energy, the detecting being detecting in the form of an image, the detecting comprising identifying echo pulses of the transmitted pulses, the echo pulses being generated as the transmitted pulses are reflected by the single domain particles; and a discriminator configured to identify in the echo pulses the electron paramagnetic response of the single domain particles.

* * * * *